(12) United States Patent
Timmins

(10) Patent No.: US 8,367,400 B2
(45) Date of Patent: Feb. 5, 2013

(54) CULTURE VESSEL ALLOWING LARGE IN SITU SCALE UP

(75) Inventor: Mark R. Timmins, No. Chelmsford, MA (US)

(73) Assignee: Corning Incorporated, Corning, NY (US)

(*) Notice: Subject to any disclaimer, the term of this patent is extended or adjusted under 35 U.S.C. 154(b) by 118 days.

(21) Appl. No.: 12/408,784

(22) Filed: Mar. 23, 2009

(65) Prior Publication Data

US 2009/0239291 A1 Sep. 24, 2009

Related U.S. Application Data

(60) Provisional application No. 61/038,458, filed on Mar. 21, 2008.

(51) Int. Cl.
*C12M 1/00* (2006.01)
*C12M 3/00* (2006.01)

(52) U.S. Cl. ............ 435/289.1; 435/286.1; 435/294.1; 435/299.1

(58) Field of Classification Search ............... 206/219, 206/484, 438, 439; 435/286.1–286.2, 289.1, 435/294.1, 297.1–297.3, 304.1, 305.1–305.4, 435/299.1, 301.1, 401
See application file for complete search history.

(56) References Cited

U.S. PATENT DOCUMENTS

| | | | | |
|---|---|---|---|---|
| 5,017,490 A | * | 5/1991 | Taiariol et al. | 435/401 |
| 5,287,961 A | * | 2/1994 | Herran | 206/219 |
| 6,024,220 A | * | 2/2000 | Smith et al. | 206/484 |
| 6,364,864 B1 | * | 4/2002 | Mohiuddin et al. | 604/410 |
| 2004/0134802 A1 | * | 7/2004 | Inoue et al. | 206/219 |
| 2008/0107781 A1 | * | 5/2008 | Carroll | 426/128 |

FOREIGN PATENT DOCUMENTS

WO  WO2004/108404  * 12/2004

* cited by examiner

*Primary Examiner* — Michael Marcheschi
*Assistant Examiner* — Shanta G Doe
(74) *Attorney, Agent, or Firm* — Hoffmann & Baron, LLP

(57) ABSTRACT

The present invention, in one aspect, provides a culture vessel which includes a body having at least a first edge at least partially perimetrically bounding the body, and at least a first seal extending from the first edge. The first seal is breachable and fluid-tight, and disposed obliquely to the first edge so as to subtend an acute angle therewith. The first seal separates the body into first and second chambers. Advantageously, with the subject invention, a culture vessel is provided which allows for volume expansion in situ.

14 Claims, 2 Drawing Sheets

CULTURE VESSEL ALLOWING LARGE IN SITU SCALE UP

CROSS-REFERENCE TO RELATED APPLICATION

This application claims priority of U.S. Provisional Patent Application No. 61/038,458, filed Mar. 21, 2008, the entire contents of which are hereby incorporated by reference.

FIELD OF THE INVENTION

The present invention relates to a device for cell and/or tissue culture production, and more particularly to a culture vessel or system of vessels which allows in situ scalability of cell cultures.

BACKGROUND OF THE INVENTION

Tissue culture vessels are used in the laboratory for many purposes. Typically, these vessels are used to culture microorganisms or tissues in a culture medium or agar which is adhered to an interior surface of the vessel.

Cell culture vessels which allow expansion into multiple additional connected vessels are known; however, traditional expansion changes the overall footprint of the culture. The traditional method entails a seed culture in a small T-flask, followed by a series of passages into even larger vessels. However, this procedure is not only a highly laborious process, but each passage represents a significant chance for contamination into the culture. Further, using multi-level, rigid plastic culture devices are unsatisfactory, as there is no way to prevent media from being contained to a select subset of the culture layers. Further, these multi-layered plastic vessels do not scale linearly, thus suggesting there may be an issue with oxygen transport. Other known existing products pose short-comings as well. For example, prior art culture cassettes are not designed to allow for in situ expansion.

Prior art expansion vessels have used a longitudinal divider for separating expansion chambers. While these expansion vessels are suitable for projects which require only a limited increase, they are unsuitable to expand vessels such that the relative expansion is on a larger order.

SUMMARY OF THE INVENTION

The present invention, in one aspect, provides a culture vessel which includes a body having at least a first edge at least partially perimetrically bounding the body, and at least a first seal extending from the first edge. The first seal is breachable and fluid-tight, and disposed obliquely to the first edge so as to subtend an acute angle therewith. The first seal separates the body into first and second chambers. Advantageously, with the subject invention, a culture vessel is provided which allows for volume expansion in situ.

In a further aspect, the subject invention provides a culture vessel assembly which includes a body having at least one edge perimetrically bounding the body; at least one breachable, fluid-tight seal extending from a first of the edges, the seal separating the body into first and second chambers; and, a port in communication with the first chamber, the collective volume of the first and second chambers being more than twice the volume of the first chamber.

In yet a further aspect, the subject invention provides a culture vessel assembly which includes a body; and, at least a first seal. The first seal is breachable and fluid-tight, and arranged to extend continuously to perimetrically bound a first chamber within the body.

These and other features of the invention will be better understood through a study of the following detailed description and accompanying drawings.

DETAILED DESCRIPTION

Figure 1:
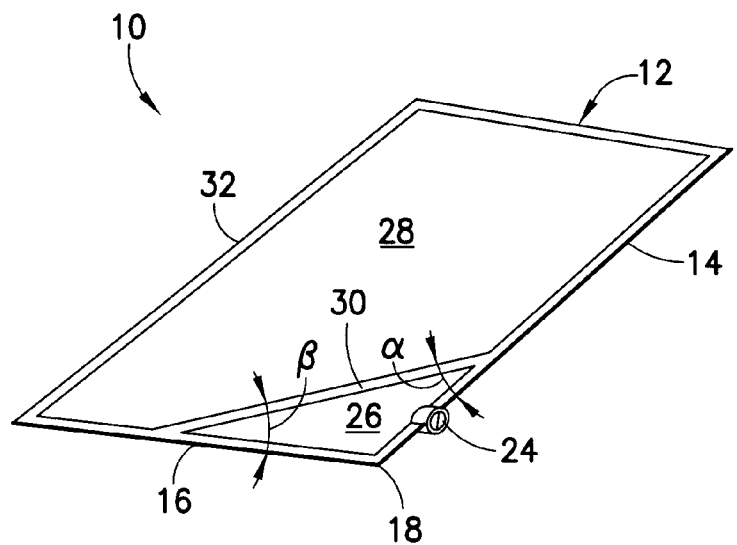
FIG. 1 is a perspective view of a culture vessel formed in accordance with the subject invention.

FIG. 1 illustrates a cell culture vessel 10. The cell culturing vessel 10 of the present invention allows for volume expansion in situ during cell culturing. The culture vessel 10 can be of any shape or configuration desired, including spherical, tubular, boxed, or any other shape. It is preferred that the culture vessel 10 be elongated and generally rectangular formed to extend along a longitudinal axis. Preferably, the culture vessel 10 has a body 12, having at least a first edge 14, which at least partially perimetrically bounds the body 12 of the culture vessel 10. The cell culturing vessel 10 may be made of any material desired. Preferably, the body 12 is made of a plastic material, and more preferably is made of a thin, deformable plastic. In a preferred embodiment, the culturing vessel 10 is of a flexible bag construction. As will be appreciated by those skilled in the art, the culturing vessel 10 is formed of materials compatible with cell culturing. Optionally, the body 12 may include a plurality of edges, including second edge 16 intersecting with, and extending from the first edge 14. A corner 18 may be defined at the intersection of the first and second edges 14 and 16.

Figure 2:
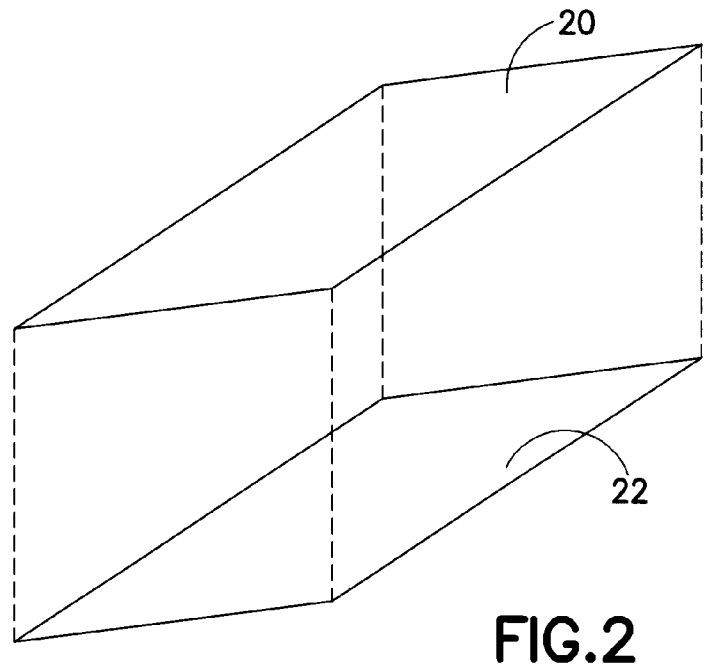
FIG. 2 is a schematic of a possible assembly of a culture vessel useable with the subject invention.

The body 12 may be formed by any known technique. With reference to FIG. 2, the body 12 may be formed by placing first and second sheets 20, 22 one atop the other. Portions of the sheets 20, 22, preferably the edges (such as the first and second edges 14 and 16) are joined to collectively form the body 12. The sheets 20, 22 may be joined using any known technique, such as fusion bonding, adherent bonding, mechanical affixing and combinations thereof. It is preferred that a fluid-tight perimeter be defined about the body 12 to permit cell growth medium to be contained therein. As shown in FIG. 1, a port 24 is provided to obtain access to the interior of the body 12 within the sealed perimeter.

The culture vessel 10 allows for compartmental expansion within the culture vessel 10. The culture vessel 10 is separated into a plurality of compartments or chambers 26, including at least a first chamber 26 and a second chamber 28, with each of the chambers 26, 28 being preferably bounded by edges (such as the first and second edges 14, 16), of the body 12 and at least one internal seal 30. The chambers may be formed to generally have the same thickness (can be taken as the spacing between the sheets 20, 22), excepting out boundary effects (such as, reduced spacing near the edges). As will be recognized by those skilled in the art, there may be any number of chambers in the culture vessel 10.

One or more of the seals 30 separating the chambers 26, 28 are preferably disposed obliquely to the first edge 14 of the vessel 10 so as to subtend an acute angle α therewith, as shown in FIG. 1. Optionally, one or more of the seals 30 may extend from the first edge 14 to the second edge 16. Preferably, the second edge 16 is disposed obliquely to the seal(s) 30 and subtends an acute angle β therewith.

The seals 30 may be arranged to extend across the body 12 in various patterns. For example, one of the seals 30 may extend from, and be disposed obliquely to, the first edge 14, and extend to a third edge 32 of the body 12 located opposite the first edge 14. With the first edge 14 being at least partially arcuate, the seals 30 may be formed to extend therefrom. With the seals 30 extending from an arcuate edge, the seals 30 may be considered to extend obliquely therefrom (even with the seals 30 being arranged as a radius or radii on the vessel 10). It can be taken that the seals 30 are oblique to the arcuate edge, even if the seals 30 are perpendicular or generally perpendicular to a tangent disposed along the arcuate edge.

There may be any number of the seals 30 in the body 12. The seals 30 are preferably fluid-tight. The seals 30 may be formed by any means which provides a fluid-tight sealing effect. Preferably, the seals 30 are defined by heat bonded, fused portions of the body 12 (e.g., fused portions of the sheets 20, 22). In addition, or alternatively, the seals 30 may be formed by adherently joined portions of the body 12 and/or by cooperating interlocking members. The seals 30 may be formed as removable elements, such as removable septums.

To allow for compartmental expansion, the seals 30 are breachable. Preferably, the seals 30 are breached by causing rupturing thereof. Such rupturing may be achieved by forming the seals 30 to be more readily rupturable than the body 12. With this arrangement, sufficient pressure applied to one or both of the chambers 26, 28 about the seal 30 desired to be breached, results in rupturing of the seal 30 and fluid communication of the chambers 26, 28, with the surrounding portions of the body 12 remaining intact.

Figure 3:
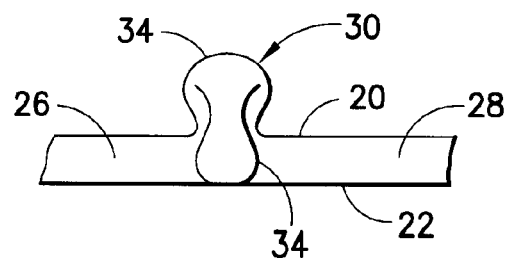
FIG. 3 is a partial cross-sectional view showing interlocking members forming a seal; and, FIGS. 4-6 depict possible seal arrangements.

The seals 30 may also be defined by joined interlocking members 34. With reference to FIG. 3, the interlocking members 34 may be of any known type which permits linear fluid-tight seals to be defined. As shown in FIG. 3, one of the interlocking members 34 may be mounted to the sheet 20 and another of the interlocking members 34 may be mounted to the sheet 22. The interlocking members 34 may be formed to be single-use or reversibly re-engageable to repeatedly open and close the seal 30. A slide mechanism or tool may be utilized to facilitate separation of the interlocking members 34. With the use of the interlocking members 34, the seals 30 are breached by causing separation thereof. Breach of the seals 30 results in communication of the chambers (e.g., the chambers 26, 28) separated by the seals 30. As will be recognized by those skilled in the art, the seals 30 may be formed by any means (fused portions; adhesive; mechanical elements), including combinations of means, such as the seal arrangements described above.

The vessel 10 optionally includes the port 24 preferably leading into the first chamber 26, through which cell-growth media or cell tissue may be inserted into the vessel 10. The port 24 may be an air-tight or vented port and must be capable of sealing the vessel 10 once the desired material is inserted into the vessel 10. There may optionally be several ports leading into the vessel 10, which may be located at various places on the vessel 10 to permit communication with one or more of the chambers.

The vessel 10 of the present invention allows for volume expansion in situ. Preferably, chambers are provided in the body 12 which, with the seals 30 being breached, provide for significant volume expansion. Preferably, the breach of one of the seals 30 permits two of the chambers, such as the first and second chambers 26, 28, to come into communication resulting in the collective volume of the two chambers being at least twice as great as the volume of the initial sealed chamber. For example, with reference to FIG. 1, with the first chamber 26 being used initially for cell culturing, upon breach of the seal 30, the first chamber 26 comes into communication with the second chamber 28. It is preferred that the collective volume of the first chamber 26 and the second chamber 28 be at least as twice as great as the volume of the first chamber 26, preferably more than twice the volume of the first chamber 26. In this manner, cell cultures can be iteratively grown in ever-greater volumes.

Figure 5:
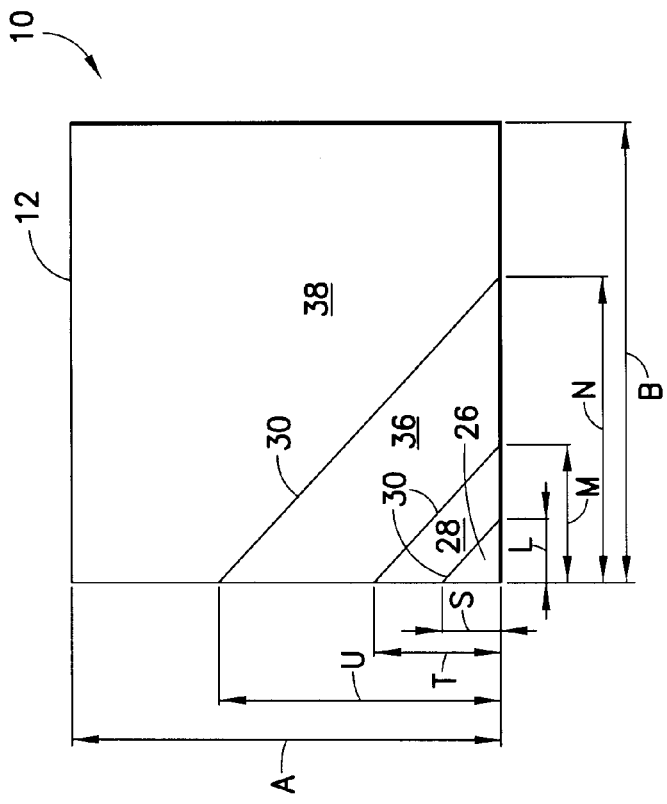
Figure 4:
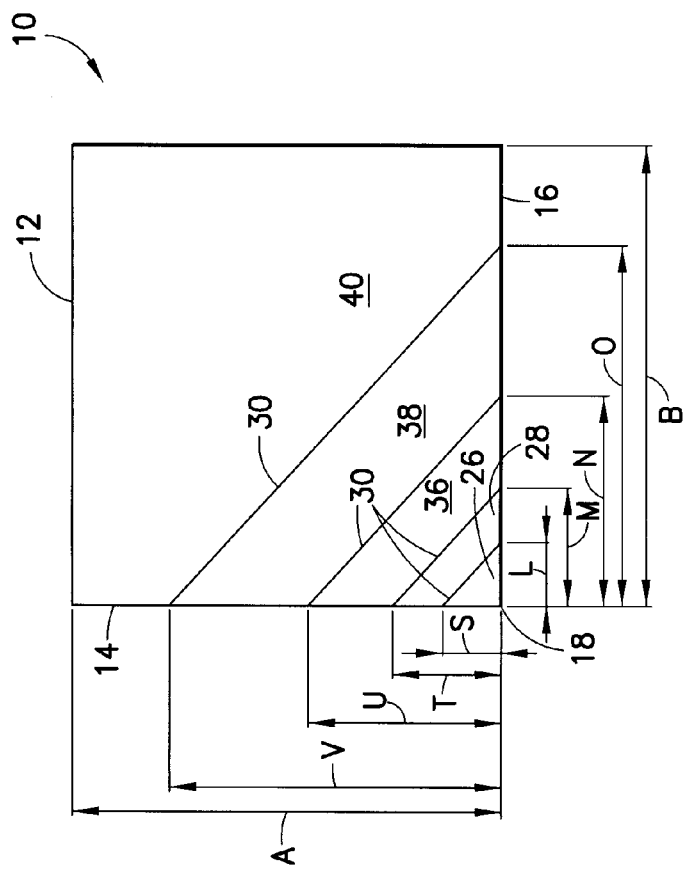

With reference to FIGS. 4 and 5, various arrangements for the seals 30 are depicted. With the vessel 10 having a generally rectangular shape, and with the seals 30 being arranged in the preferred oblique arrangement described above, triangular-shaped chambers may be defined in the body 12.

The seals 30 may be arranged to provide a constant rate of expansion upon breach of the seals. For example, with reference to FIG. 4, in addition to the first and second chambers 26 and 28, a third chamber 36, a fourth chamber 38 and a fifth chamber 40 may be defined in the body 12 by the seals 30. In an initial state, the first chamber 26 is first utilized, for example, having all necessary materials for cell culturing being provided therein through the port 24. To allow for incremental expansion from the first chamber 26 at a constant rate, the seals 30 defining the first through fifth chambers 26, 28, 36, 38 and 40, may be disposed as set forth in Table 1.

TABLE 1

|  | Seal Separating First and Second Chambers (Spacings S, L) | Seal Separating Second and Third Chambers (Spacings T, M) | Seal Separating Third and Fourth Chambers (Spacings U, N) | Seal Separating Fourth and Fifth Chambers (Spacings V, O) |
| --- | --- | --- | --- | --- |
| First Edge Location* (as %-age of overall length A) | 14.1 | 24.5 | 45 | 77 |
| Second Edge Location* (as %-age of overall length B) | 14.1 | 24.5 | 45 | 77 |

*Measured in direction away from the corner 18

The arrangement of the seals 30 as set forth in Table 1 allows for generally four half-log expansions (approximately 3.2×) increases in volume. As such, not only does each expansion provide a greater than twice-the-size volume, but the expansions increase is at a constant rate. For example, with the arrangement of Table 1, the collective volume of the first and second chambers 26, 28 is approximately 3.2 times greater than the volume of the first chamber 26, and the collective volume of the first, second and third chambers 26, 28 and 36 is approximately 3.2 times greater than the collective volume of the first and second chambers 26, 28, and so forth. Table 2 sets forth approximate volumes achievable with the seal arrangement of Table 1.

TABLE 2

| | |
|---|---|
| Volume of First Chamber | 1 |
| Volume of First and Second Chambers | 3 |
| Volume of First, Second and Third Chambers | 10 |
| Volume of First, Second, Third and Fourth Chambers | 30 |
| Volume of First, Second, Third, Fourth and Fifth Chambers | 100 |

Note:
Volume is determined by area defined by seals with unit thickness.

It is preferred that the seals 30 be located within about 14%-77% of the overall length of the respective edges (e.g., the edges 14, 16) as measured away from the corner 18. Although Table 1 sets forth equal spacings along the edges 14, 16 for the seals 30, the seals 30 may be located at different spacings along the edges.

As will be readily recognized by those skilled in the art, other seal arrangements are possible. For example, with reference to FIG. 5, four chambers are utilized (chambers 26, 28, 36 and 38) with the seals 30 being disposed as set forth in Table 3.

TABLE 3

| | Seal Separating First and Second Chambers (Spacings S, L) | Seal Separating Second and Third Chambers (Spacings T, M) | Seal Separating Third and Fourth Chambers (Spacings U, N) |
|---|---|---|---|
| First Edge Location* (as %-age of overall length A) | 14.1 | 30 | 66 |
| Second Edge Location* (as %-age of overall length B) | 14.1 | 30 | 66 |

The arrangement of the seals 30 in Table 3 allows for approximately constant 4.6× increments in volume. Table 4 sets forth the approximate obtainable volumes.

TABLE 4

| | |
|---|---|
| Volume of First Chamber | 1 |
| Volume of First and Second Chambers | 4.6 |
| Volume of First, Second and Third Chambers | 21.5 |
| Volume of First, Second, Third and Fourth Chambers | 100 |

Note:
Volume is determined by area defined by seals with unit thickness.

It is preferred to have the increased expansion result in constant volume-to-surface ratios. This is important for adherent cell growth.

The vessel 10 may be formed with a rigid construction with the seals 30 being removable, rigid dividers. In addition, the vessel 10 may be formed (e.g., with appropriate valving) to be coupled in series with other vessels to permit not only chamber-to-chamber expansion, but also vessel-to-vessel expansion. With a serial arrangement, various combinations of vessel and chamber expansion may be utilized.

Figure 6:
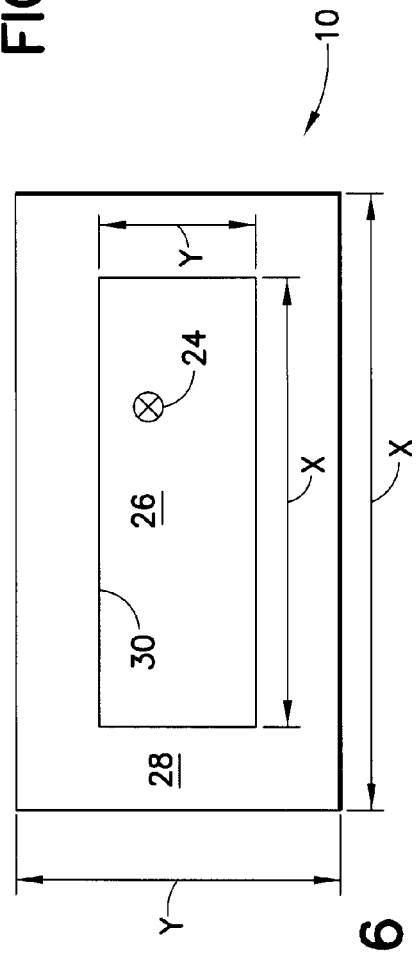

As a further embodiment, and with reference to FIG. 6, the chambers may be arranged in a fully or partially nested fashion, preferably in a fully nested fashion. By way of non-limiting example, the first chamber 26 may be located at least partially within the second chamber 28. One of the seals 30 may be arranged to be continuous to define a fluid-tight barrier between the first and second chambers 26, 28. For expansion, the seal 30 is caused to rupture with the first and second chambers 26, 28 coming into communication. It is preferred that the relative volumes of the first and second chambers 26, 28 be configured as discussed above. It is further preferred that the expansion be conducted from the innermost chamber (e.g., the first chamber 26) and be conducted outward therefrom (e.g., to the second chamber 28). As such, it is preferred that the port 24 be in communication with the innermost chamber (e.g., the first chamber 26). A third or more chamber(s) (e.g., the third chamber 36) may be also utilized.

By way of non-limiting example, to permit an at least two-fold volume increase upon expansion with a nested arrangement, it is preferred that the length and width of each smaller nested chamber be approximately 71% the length and width of the chamber surrounding the smaller nested chamber. With this arrangement, and with reference to FIG. 6, the length x of the first chamber 26 is approximately 71% the length x of the second chamber 28. Likewise, the width y of the first chamber 26 is approximately 71% of the width y of the second chamber 28. This arrangement provides for an at least two-fold increase in volume upon breach of the seal 30 separating the first and second chambers 26, 28. This same dimensional arrangement can be provided to the second and third chambers 28, 36, and so forth, to maintain an at least two-fold volume increase with each successive expansion.

What is claimed is:

1. A culture vessel for adherent cell growth in situ comprising:
    a body having at least a first edge at least partially perimetrically bounding said body;
    a first seal extending from said first edge, said first seal being breachable and fluid-tight, and disposed obliquely to said first edge so as to subtend an acute angle therewith, said first seal separating said body into first and second chambers; and,
    a second seal which separates said second chamber from a third chamber, said second seal being breachable and fluid-tight, said second chamber contiguously contacting said first and second seals,
    wherein, the collective volume of said first, second and third chambers is at least twice the collective volume of said first and second chambers; and
    wherein, said first chamber, said second chamber, said third chamber, said first seal and said second seal are configured to provide a constant rate of expansion of the collective volumes with the ratio of the collective volume of said first and second chambers to the volume of said first chamber being equal to the ratio of the collective volume of said first, second and third chambers to the collective volume of said first and second chambers, and to provide a constant rate of volume to surface ratio with the ratio of volume to surface area of said first chamber being equal to the ratio of the collective volume of said first and second chambers to the collective surface area of said first and second chambers, and equal to the ratio of the collective volume of said first, second and third chambers to the collective surface area of said first, second and third chambers.

2. The culture vessel of claim 1, wherein said first seal is more readily rupturable than said body, said first seal being breached by causing rupture thereof.

3. The culture vessel of claim 1, wherein said first seal is formed by fused portions of said body.

4. The culture vessel of claim 1, wherein said first seal is formed by adherently joined portions of said body.

5. The culture vessel of claim 1, wherein said first seal is formed by joined interlocking members, said first seal being breached by separating said joined interlocking members.

6. The culture vessel of claim 1, further comprising a port in communication with said first chamber.

7. The culture vessel of claim 1, wherein said culture vessel is a flexible bag.

8. The culture vessel of claim 1, wherein the collective volume of said first and second chambers is at least twice the volume of said first chamber.

9. The culture vessel of claim 1, wherein said body includes a second edge intersecting with, and extending from, said first edge, said first seal extending from said first edge to said second edge.

10. The culture vessel of claim 9, wherein said first and second edges intersect at a first corner, said first seal being located on said first edge at a point located at about 14%-77% of the total length of said first edge as measured away from said first corner, and said first seal being located on said second edge at a point located at about 14%-77% of the total length of said second edge as measured away from said first corner.

11. The culture vessel of claim 1, wherein said first edge is at least partially arcuate.

12. The culture vessel of claim 1, wherein said second seal is disposed obliquely to said first edge so as to subtend an acute angle therewith.

13. The culture vessel of claim 1, wherein said first and second seals are generally parallel.

14. The culture vessel of claim 1, wherein said first chamber is located at least partially within said second chamber.

\* \* \* \* \*